United States Patent
Cao et al.

(10) Patent No.: US 8,999,923 B2
(45) Date of Patent: Apr. 7, 2015

(54) HEAT-STABLE, AQUEOUS LACTOFERRIN COMPOSITION AND ITS PREPARATION AND USE

(75) Inventors: Linqiu Cao, Wageningen (NL); Hans Maas, Gemert (NL)

(73) Assignee: Campina Nederland Holding B.V., Zaltbommel (NL)

( * ) Notice: Subject to any disclaimer, the term of this patent is extended or adjusted under 35 U.S.C. 154(b) by 862 days.

(21) Appl. No.: 12/999,292

(22) PCT Filed: Jun. 15, 2009

(86) PCT No.: PCT/NL2009/050342
§ 371 (c)(1),
(2), (4) Date: Mar. 4, 2011

(87) PCT Pub. No.: WO2009/154447
PCT Pub. Date: Dec. 23, 2009

(65) Prior Publication Data
US 2011/0172160 A1 Jul. 14, 2011

(30) Foreign Application Priority Data

Jun. 16, 2008 (EP) .................... 08158354

(51) Int. Cl.
*A61K 38/40* (2006.01)
*A23L 1/305* (2006.01)
*A61K 9/08* (2006.01)
*A61K 47/26* (2006.01)

(52) U.S. Cl.
CPC ............... *A61K 38/40* (2013.01); *A23L 1/3056* (2013.01); *A23V 2002/00* (2013.01); *A23V 2250/54248* (2013.01); *A23V 2250/606* (2013.01); *A23V 2250/61* (2013.01); *A23V 2250/628* (2013.01); *A23V 2250/64* (2013.01); *A61K 9/08* (2013.01); *A61K 47/26* (2013.01)

(58) Field of Classification Search
USPC ...................................... 514/2.5, 23
IPC .................. A61K 38/40; C07K 14/79
See application file for complete search history.

(56) References Cited

U.S. PATENT DOCUMENTS

2007/0161541 A1  7/2007  Kruzel et al.

FOREIGN PATENT DOCUMENTS

| EP | 0 437 857 A1 | 7/1991 |
| EP | 0 437 958 | 7/1991 |
| EP | 0 454 084 A1 | 10/1991 |
| EP | 1 040 766 A1 | 10/2000 |
| EP | 1 116 490 A1 | 7/2001 |
| EP | 1 166 653 A2 | 1/2002 |
| GB | 2 361 703 | 10/2001 |
| WO | WO 2006/098625 | 9/2006 |

OTHER PUBLICATIONS

Brisson, et al. "Effect of iron saturation on the recovery of lactoferrin in rennet whey coming from heat-treated skim milk", J. DAIR SCI., Jun. 2007, vol. 90, Issue 6, pp. 2655-2664.
International Search Report mailed Jul. 16, 2009 in PCT/NL2009/050342.
International Preliminary Report on Patentability mailed Jul. 14, 2010 in PCT/NL2009/050342.

*Primary Examiner* — David Lukton
(74) *Attorney, Agent, or Firm* — Gilberto M. Villacorta; Sunit Talapatra; Foley & Lardner LLP

(57) ABSTRACT

The invention pertains to an aqueous composition containing lactoferrin, 35-70 wt % carbohydrate and/or polyol stabilizers, based on the total weight of the aqueous composition, said composition exhibiting a pH higher than 2, lower than 5. At these 5 conditions, the aqueous composition and lactoferrin contained therein may be subjected to a heat treatment without significantly affecting the physiological activity of the lactoferrin. The invention thus particularly pertains to the above aqueous composition, being heat-treated, thus containing heat-stabilized lactoferrin.

12 Claims, 2 Drawing Sheets

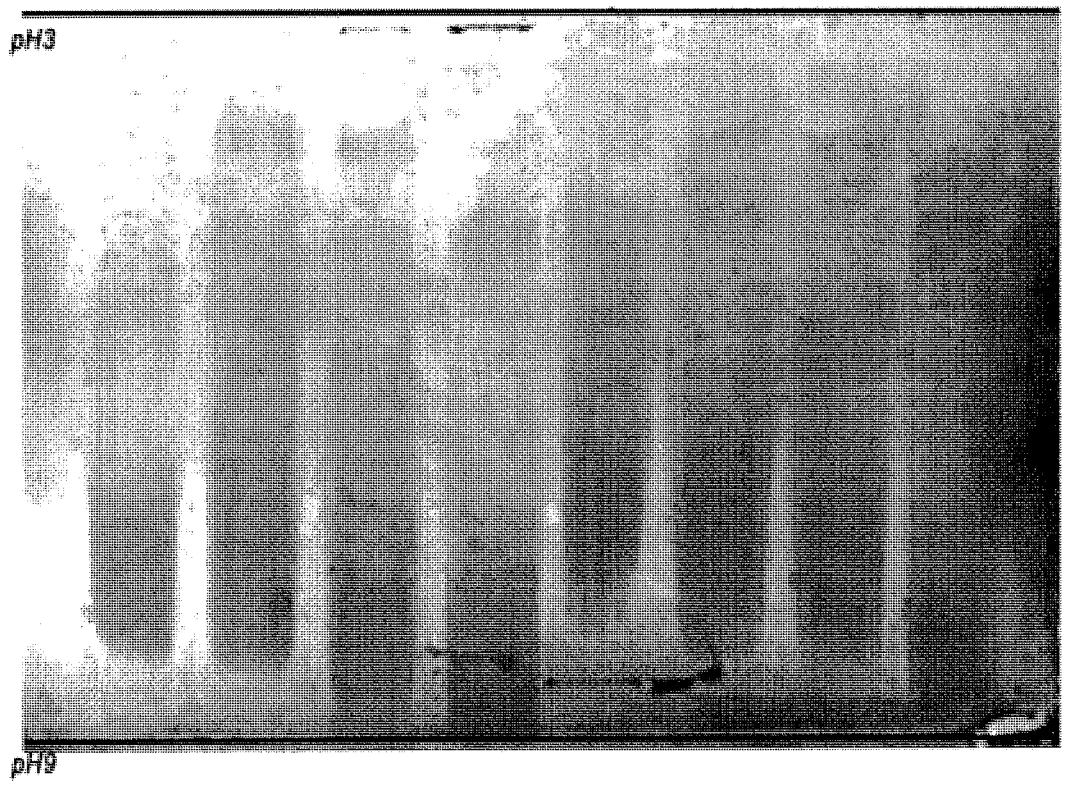

HEAT-STABLE, AQUEOUS LACTOFERRIN COMPOSITION AND ITS PREPARATION AND USE

This application is a 371 of PCT/NL09/50342, filed Jun. 15, 2009, which claims foreign priority to EP 08158354.4, filed Jun. 16, 2008.

FIELD OF THE INVENTION

The present invention pertains to a method for heating lactoferrin without losing physiological activities, and extending its shelf-life in liquid formulations. More particularly, the present invention relates to a method for heating lactoferrin at acidic conditions at a temperature over 60° C. The invention also pertains to the use of the lactoferrin thus treated.

BACKGROUND OF THE INVENTION

Lactoferrin is known as an iron-binding protein distributed in tear, saliva, peripheral blood, milk and the like. It has been known that lactoferrin has various physiological activities, for example, antibacterial activity against harmful bacteria, activity for promoting iron absorption at the intestine, anti-flammatory activity and so on. A review of the usefulness of lactoferrin is given in US-A-2007/161541, its contents hereby incorporated by reference.

Therefore addition of lactoferrin to foods, processed foods, medicines, cosmetics and the like or direct intake as supplement is desirable. These products generally need to be heat-treated e.g. pasteurized or sterilized, to render them microbially safe and shelf-stable for a longer time.

However, if no measures are taken, lactoferrin will show unstable to heating, and heat treatment of lactoferrin may result in denaturation of lactoferrin at physiological pH. It is reported in the art that the physiological activities of lactoferrin are almost lost by heating at 62.5° C. for 30 minutes, and complete denaturation is occurred by heating at 70° C. for 15 minutes.

As is clear from above, sufficient thermal treatment could not be applied to lactoferrin as an ingredient for utilizing its physiological activities. A liquid formulation or a stock solution of lactoferrin has to be subjected to sterilisation, in order to obtain a long shelf-life (several weeks or months before consumption).

EP 454.084 and EP 1.040.766 both teach iron-enriched lactoferrin beverages. Iron fortification is needed for persons having an anemic drift, pregnant women or nursing mothers. Although it may not be explicitly mentioned there, the skilled person immediately recognizes the effect of iron saturation on the recovery of lactoferrin aimed for in EP'084 and EP'766. According to Brisson et al. "Effect of iron saturation on the recovery of lactoferrin in rennet whey coming from heat-treated skim milk" J. Dairy Sci. 90: 2655-2664, the lactoferrin complexes with iron, which complexation improves its thermal stability. However, the use of iron in nutritional fields is often not desirable, for instance from a taste perspective. Also, iron complexation may add to the stability of the lactoferrin, but over time denaturation may still arise. Hence, a need exists for additional and improved methods to achieve heat stabilisation.

GB 2,361,703 teaches stabilisation of vitamin B12 and/or folic acid by complexing it with lactoferrin, thus increasing the shelf life of folic acid and vitamin B12, otherwise exhibiting low heat and storage stability in the presence of oxygen. Lactoferrin is used from any source, including iron-stablized lactoferrins. However, if looking from a different perspective, i.e. searching for ways to stabilize lactoferrin, the solution to bind it to folic acid and vitamin B12 for use in foodstuffs is an undesirable one. These compounds are expensive, interfere in all kinds of metabolic pathways; related therewith, administration of these compounds to people is not unrestricted.

In order to address its heat stability, it is suggested in EP-A-437.958, in the name of Morinaga Milk Industry, to heat lactoferrin at a temperature over 60° C. at a pH between 1.0-6.5. From liquid chromatography results listed in table 1 therein, it is concluded that lactoferrin is stable when heated for 5 minutes at 60° C. under acidic conditions. The very same table also shows that the window of success dramatically narrows when increasing the temperature to 70, 80, 90 or even 100° C. Above 100° C., all lactoferrin is denaturated. All measurements are taken shortly after heat treatment. EP-A-437.958 is silent on stability of the lactoferrin over time and storage temperature The contents of EP-A-437.958 is herein incorporated by reference.

In an attempt to reproduce the results reported in EP-A-437.958, the inventors found that HPLC (high performance liquid chromatography) is in fact unsuited to determine the degree of denaturation. It was found that a better technique involves FPLC (Fast performance liquid chromatography) and/or ELISA, and that HPLC readily overestimates the degree of "undenaturation". Hence, the results in table 1 of EP-A-437.958 are in reality not as good as claimed. Moreover, it was found that heat-stable lactoferrin in EP-A-437.958, if achieved at all, was short-lasting. Denaturation still occurred, under a prolonged storage time under certain temperatures within weeks. EP-A-437.958 itself is silent on the effect of heat treatment on shelf-life. Further, the limited success of the method advocated by Morinaga dramatically decreases when extending the heating times. This is in fact acknowledged in the recited patent itself. The observations in this paragraph are founded in the comparative examples accompanying the present invention. Finally, the present inventors observed that the method of EP-A-437.958 produces aqueous lactoferrin containing compositions that are only stable for longer time periods if kept at 7° C. or lower, thus necessitating a cooling system.

Concluding, the alleged heat-stability of lactoferrin by heat-treating it at acidic conditions in accordance with EP-A-437.958 is fairly limited, since product lines in practice often involve more severe combinations of heating time and temperature, in pasteurization. Often, use is made of boiling water, and especially in batch production heating times may easily extend. In addition, should it be required to keep the aqueous lactoferrin composition stable for longer time, e.g. months, it involves expensive and logistically difficult-to-operate cooling systems. Many applications or nutritional formulations containing lactoferrin should have a shelf-life of weeks, even months. The above method cannot fulfil this condition.

The inventors of the present invention have exerted their efforts to develop an improved method for heating lactoferrin without losing its physiological activities, and resulting in a heat-treated lactoferrin that remains stable over extended time periods, including storage temperatures above 7° C. Also, the inventors wanted to refrain from being restricted to complexing lactoferrin with iron or compounds such as vitamin B12 and folic acid.

SUMMARY OF THE INVENTION

It is an object of the present invention to provide a method for heat treatment of lactoferrin (LF) without losing physiological activities thereof, such as antibacterial activity, iron-binding activity, antigenicity. Such a heat-stabilising method should hold over extended heating times and at high temperatures, and the resulting lactoferrin should remain stable over extended times, in terms of weeks or even months. It is also an object to provide a method for heating lactoferrin that results in heat-stabilisation of lactoferrin upon storage for extended periods at higher temperatures, above 7° C.

It was found that these objects are achieved if lactoferrin is heated under acidic conditions in the presence of large amounts of hydrophilic carbohydrate or polyol stabilizers. The high level of stabilizers causes the lactoferrin to be stable in acid solution for a very long time, at least two weeks, preferably at least four weeks, depending on the storage temperature and pH of the solution. The heating step destroys residual proteases that otherwise cause degradation of lactoferrin upon storage.

The successful interplay between the lactoferrin and sugars at high temperature is restricted to a pH higher than 2, and lower than 5. At low pH, acidic degradation or hydrolysis of lactoferrin comes into play, as can be demonstrated with FPLC. At the upper pH boundary, heat stabilisation stays behind and Maillardation, induced by the significant amounts of sugars present, starts to interfere.

Although the examples of EP-A-437.958 disclose sugars being present during heat-treatment, these are clearly not part of the invention there. The sugars are merely present as an additional food ingredient, e.g. orange juice. As evidenced in the accompanying examples, at the low levels presented in EP-A-437.958, no effect of the sugars could be observed. In fact, example 5 of EP-A-437.958 teaches a gel, and not a liquid formulation in accordance with the present invention. The effects of instabilities are less pronounced for these cases. It is now found that an amount of carbohydrate or polyol stabiliser, i.e. sugars higher than 30 wt % is essential to heat-stabilize lactoferrin in liquid formulations.

This way, the inventors have rendered it possible to provide sterilized liquid LF-containing formulations that are shelf-stable. Up to present, LF-containing solutions suffered from low shelf-stability. The commercial alternative remaining was to provide LF in the form of spray-dried powders. Advantageously, the manufacture of liquid sterilized shelf-stable LF compositions now available requires less energy (evaporation of solvent redundant). Also, the sterilized form makes simple aseptic addition to various formulations, e.g. infant formulae, within reach. The liquid formulation can be directly used in end formulations, without the need for dissolution.

BRIEF DESCRIPTION OF THE DRAWINGS

FIG. 1 shows results of the protective effect of sugar during heat-treatment by iso-electro-focusing gel electrophoresis between pH 3 and 9.

DETAILED DESCRIPTION OF THE INVENTION

Figure 2A:
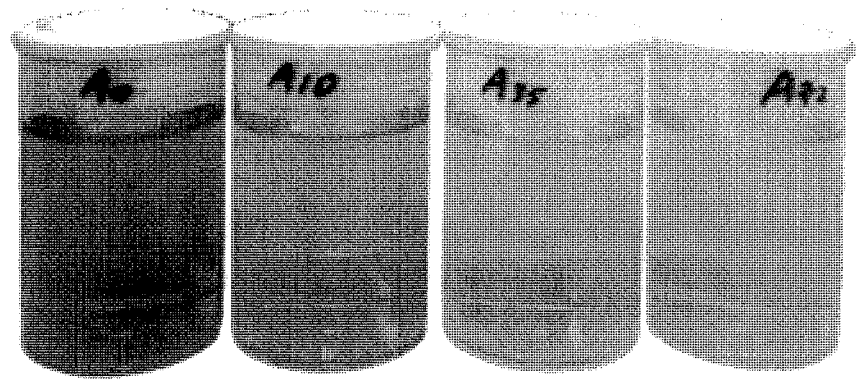
FIG. 2 shows the differences in color among embodiments of the invention after LF heat-treatment.

The invention thus pertains to an aqueous composition containing lactoferrin, 35-70 wt % carbohydrate and/or polyol stabilizers, based on the total weight of the aqueous composition, said composition exhibiting a pH higher than 2, lower than 5. At these conditions, the aqueous composition and lactoferrin contained therein may be subjected to a heat treatment without significantly affecting the physiological activity of the lactoferrin. The invention thus particularly pertains to the above aqueous composition, being heat-treated, thus containing heat-stabilized lactoferrin. This way, heat-stablized lactoferrin is provided without the need for complexation.

In another aspect the invention pertains to a method of preparing a heat-stabilized lactoferrin-containing composition according to the present invention, by a) providing an aqueous composition containing lactoferrin, 35-70 wt % carbohydrate and/or polyol stabilizers, based on the total weight of the aqueous composition, said composition exhibiting a pH higher than 2, lower than 5, and b) subjecting said aqueous composition to a heat treatment, preferably at a temperature of at least 60° C.

In yet another aspect, the invention pertains to the use of the heat-stabilized aqueous lactoferrin-containing composition in (health) food, feed, nutritional supplements, cosmetics, medicines, and to such (health) food, feed, nutritional supplements, cosmetics and medical products containing the heat-stabilized lactoferrin. The lactoferrin of the present invention finds particular use in infant formulae, medical nutrition, sports foods, health foods and supplements, for instance in beverages, yoghurt and yoghurt drinks. Furthermore, the LF- and sugar-containing solution can also be used as a supplement without further treatment other than the aforediscussed heat treatment.

The heat-stabilized lactoferrin clearly distinguishes from heat-treated lactoferrin commercially available in its long-term stability at elevated temperatures, i.e. above 7° C. Therefore, with "heat-stabilized" in the context of the invention it is meant that the physiological properties, e.g. iron binding activity, of the heat-treated lactoferrin remain significantly unchanged if the acidic composition containing said lactoferrin is stored at normal storage conditions, i.e. between 7-25° C., preferably higher than 7° C., for a period of two weeks, more preferably three weeks, most preferably four weeks. Changes in the physiological properties are monitored in terms of the degree of denaturation, using FPLC and/or ELISA, and iron binding capacity, for instance as detailed in the examples. For suitable ways to perform FPLC, ELISA and iron binding measurements, the skilled person is referred to the citations given below tables 3 and 4. There, it is also shown that both FPLC and ELISA are suited techniques to study LF content, and changes therein. Changes in the degree of denaturation of less than 5% are considered insignificant, or for that matter, within experimental error. Note that the stability of the lactoferrin heat-treated in accordance with the present invention is not restricted to the above-given time intervals, but readily extends up to months (see examples). However, the above relatively short intervals are sufficient to distinguish the heat-treated lactoferrin of the present invention from those commercially available, for instance as reported in EP-A-437.958. The heat-treated composition is preferably a heat-sterilized, e.g. UHT-processed composition. In another embodiment, the composition is cooked, i.e. treated at 100° C.

The word "lactoferrin" used herein includes lactoferrin (LF) derived from any and all sources of lactoferrin such as mammalian milk (for example, human milk as well as cow's, sheep's, goat's, horse's milk, caprine's milk, camel's milk and the like) at any lactation stage (for example, colostrum, transitional milk, matured milk, milk in later lactation), processed milk and byproducts in milk-processing such as skim milk, whey and the like (hereinafter they are referred to in general as milk and the like). It is preferred to use bovine lactoferrin.

The word "lactoferrin" used herein includes any and all lactoferrin substances such as recombinant lactoferrin; native lactoferrin just isolated by conventional methods (for example, ion-exchange chromatography) from any and all sources of lactoferrin; apolactoferrin obtained by removing iron from native lactoferrin with hydrochloric acid, citric acid and the like; metal saturated lactoferrin obtained by chelating apolactoferrin with metal such as iron, copper, zinc, manganese and the like; or suitable mixtures thereof (hereinafter they are abbreviated as LF in general).

It may be non-purified lactoferrin, i.e. lactoferrin extracted directly form either milk or lactoserum or other medium in the case of recombinant lactoferrin and not subjected to additional purification steps. Pure lactoferrin has a molecular weight expected of 78 kDa. Other high or low molecular weight minor components present in the lactoferrin composition indicate the source of lactoferrin, as will be apparent to the skilled person. In one embodiment, native lactoferrin is applied, "native" being defined as >85% native as measured using ELISA.

The term "heat-stabilized lactoferrin" as obtained using the method of the present invention encompasses those embodiments in which at least 90% of the lactoferrrin present is still stable, preferably native, after heat treatment, preferably at least 95%. These numbers can be readily determined using ELISA, FPLC as laid down in the specification.

If not clear from the above, the term "heat-stabilized", or for that matter "heat stability", is understood to comprise stabilization of a heat-treated LF over time, rather than stabilization of LF during heat treatment, the meaning given to this term for instance in EP-A-437.958. In the art, long-term heat-stable LF is sometimes referred to as 'storage stable heat-trated LF'. This terminology may be adopted here.

No means are taken to influence the salt strength of the lactoferrin. The ionic strength in lactoferrin-providing sources typically corresponds to a level of at least 0.01 M when dissolved in more than 10% (w/w) LF solution. The salt level is not considered a critical factor, provided that the ionic strength, particularly during heat treatment, is higher than 0.01 M. At lower levels, precipitation could occur.

The amount of lactoferrin contained in the aqueous composition is preferably in the range of 0.05-20 wt %, based on the total weight of the aqueous composition. The amount of lactoferrin is preferably at least 0.1, more preferably at least 0.5, even more preferably at least 1 wt %, most preferably at least 2 wt %. The maximum amount of lactoferrin is preferably 18 wt %, more preferably 15 wt %, even more preferably 10 wt %. The amount of lactoferrin may be adjusted in view of its subsequent application, as will be explained in more detail below.

As carbohydrate stabilizer, it is preferred to use monosaccharides, disaccharides, trisaccharides, tetrasaccharides, pentasaccharides, hexasaccharides and/or oligosaccharides, preferably containing up to 10 monosaccharide units.

Preferred examples include dextrose, fructose, sucrose, glucose, maltose, trehalose, inulin or oligofructose and/or mixtures thereof, depending on usage. Components—or even fractions thereof—with extended chain lengths may be present in the composition, but those that do not fall within the above definition of a carbohydrate stabilizer are not considered to contribute to the weight numbers according to the present invention. Alternatively or additionally, as a carbohydrate stabilizer maltodextrins or glucose syrups can be used. It is preferred that the DE (dextrose equivalents) of the carbohydrate stabilizer(s) is between 1 and 99, more preferably between 5 and 99. Suitable sources of carbohydrate stabilizer in the context of the invention are invert sugar, or corn syrup, such as HFCS (High fructose corn syrup). Invert sugar is a mixture of glucose and fructose in approximately equal weight proportions. It is preferred that the carbohydrate stabilizer contains at least 45 wt %, preferably at least 50 wt % of glucose and/or fructose, based on the total amount of carbohydrate stabilizer present in the composition. Additionally or alternatively, it is preferred that the carbohydrate stabilizer contains glucose and fructose, in relative amounts in the range of 1.5:1-1:1.5, preferably 1.2:1-1:1.2. In a preferred embodiment, the invert sugar additionally contains sucrose. In such case, it is preferred that the stabilizer contains at least 65 wt % of glucose, fructose and/or sucrose. In another embodiment, HFCS is used as a source of carbohydrate stabilizer; it is preferred to contain at least 40 wt % fructose, based on the total weight of carbohydrate stabilizer.

Suitable polyols comprise mannitol, galactitol, inositol, xylitol, sorbitol, glycerol and/or lactitol.

The amount of the aforementioned stabilizer(s) is preferably between 30 and 70 wt %, more preferably at least 35 wt %, more preferably at least 40 wt %. The amount of stabilizer (s) is preferably lower than 65 wt %, more preferably lower than 60 wt %. These numbers are based on the total weight of the aqueous composition. The effect of the amount of sugars over lesser amounts accidently applied in the art is demonstrated in the accompanying examples. At 15%, and even at 30% of sugars, lactoferrin is not provided with the shelf life stability strived for.

The aqueous lactoferrin composition is preferably a liquid formulation. The liquid has preferably a viscosity of less than 3000 mPa·s, more preferably less than 1000 mPa·s, more preferably less than 500 mPa·s, as measured using e.g a rotation viscosimeter (Brookfield) at 20° C. In a preferred embodiment, the composition thus excludes gels, where stability issues are often unnoticed.

The pH of the aqueous composition is preferably in the range of 2.5-4.5, more preferably at least pH 3. The pH of the aqueous composition is more preferably 4 or lower. A high pH gives rise to Maillard reaction, i.e. development of unappealing dark-brown discoloration and/or a bitter taste.

In accordance with the method of the present invention, pH adjustment may be achieved by adding inorganic acid (for example, hydrochloric acid, sulphuric acid, phosphoric acid and the like) and/or organic acid (for example, acetic acid, citric acid, lactic acid, fumaric acid, malic acid and the like). Certainly, when the composition per se has a pH value within the described range, pH adjustment is unnecessary, however, it is still preferable to adjust the pH of the composition of the invention to the optimum pH depending upon the heating condition to be applied (heating temperature and heating time) and the purpose of heating (for example, sterilization, cooking and the like).

The method of preparing the heat-stabilized lactoferrin-containing composition involves the mixing of water, lactoferrin and one or more of the aforementioned stabilizers, and optional pH adjustment. As a source for lactoferrin, spray-dried or freeze-dried lactoferrin may be used, or a lactoferrin-containing solution which is readily available from e.g. a lactoferrin production process. The order of mixing is not considered restrictive, provided that all steps have been completed prior to heat treatment. To improve the dispersion of lactoferrin, it can optionally be mixed with (at least part of) the stabilizer before adding water and adjusting pH.

The heat treatment, yielding the heat-treated composition according to the present invention, involves a temperature of at least 60° C., preferably at least 70° C., preferably at least 75° C., more preferably 80° C., most preferably at least 90° C. Since the lactoferrin-containing composition of the invention has proven stable over longer heating times, the heating time is not regarded particularly limited. The heat treatment preferably involves sterilization, e.g. UHT processing. Heating can be performed in various types of equipment, either batch wise or continuously. Suitable heating conditions are 15-60 seconds between 80 and 100° C. for continuous heating; 5-30 minutes between 70 and 90° C. for batch heating. A UHT step preferably involves heating between 135° C. and 150° C. for 2-35 seconds, and a batch heat treatment preferably involves heating at 80° C.-100° C. for 5-30 minutes.

In one embodiment, the heating conditions are selected in line with those presented in WO-A-03/-11040, its contents herein incorporated by reference. The heat treatment preferably comprises heating the LF-containing solution to a temperature of at least 60° C., preferably at least 70° C., and less than 200° C., more preferably less than 160° C., for a period of time equal to or at least t, which period of heating t is governed by the following formula:

$$t=(500/(T-59))-4,$$

in which t is the duration of heating (in seconds) and T is the heating temperature (in ° C.). More preferably, the maximum heating conditions complied are governed by the following formula:

$$t=(90000/(T-59))-900,$$

in which t and T have the aforesaid meaning

Heat treatment preferably involves a period of 0.1 sec to 24 hour. It is particularly preferred that the heating time ranges from 10 s-1 hour, more preferably from at least 10 minutes. The preferred corresponding minimum and maximum temperatures may be calculated from the above formulae.

Additional ingredients may be added prior or after the heating step, depending on their heat dependency and/or interaction with lactoferrin. Ingredients interfering with lactoferrin during heating may be added aseptically afterwards. Non-limiting examples of additives are vitamins, such as vitamin C, minerals, buffers, peptides, polysaccharides such as pectin, sometimes applied to activate LF, and amino acids, colorants, flavorants etc.

As mentioned above, the invention also relates to a food, feed, nutritional supplement, cosmetic or pharmaceutical product containing lactoferrin heat-stabilized by the method according to the invention. The solution can be added aseptically to a choice of products. The lactoferrin is typically present in an amount of 0.05-10 wt %, more preferably 0.1-5 wt %, based on the total weight. The LF heat-stabilized and storage-stable according to the present invention distinguishes from the prior art. Traditional heat treatment at restricted pH conditions (see e.g. EP-A-437.958) does not result in shelf-stable LF.

In one embodiment, the product is a kit of parts comprising: i) a liquid formulation comprising the heat-stabilized LF of the present invention, and ii) a liquid food formula. In liquid formulae, the LF needs to be separated from other food ingredients to avoid any interactions that may result in the loss of LF activity. The shelf properties of the LF according to the present invention now render it accessible to end users without the need for further dissolution. This is particularly advantageous in infant formulae applications (the food formula of ii) being an infant formula composition), for instance when on the road having limited access to water.

In one embodiment, the invention pertains to a method of treating acne, comprising orally administering to a person suffering from acne an effective amount of a liquid formulation comprising the heat-stabilized LF of the present invention. More details are provided in EP-A-1.833.495, its contents herein incorporated by reference. The (prophylactic) treatment may be cosmetic or non-cosmetic. Persons at risk of acne are readily identifiable for the person skilled in the art. In an embodiment, the persons at risk of or suffering from acne are teenagers, preferably between 12 and 20 years of age.

EXAMPLES

Throughout the experiments, lactoferrin was used as obtained from DMV International, The Netherlands.

Example 1

Effect of pH

The pH effect on the heat-treatment (95° C. for 45 seconds) of LF-containing syrup solution (1% LF, w/w) in sugar syrup A (46 w/w %) was studied using FPLC (Fast performance liquid chromatography). Sugar syrup A comprises a mixture of glucose:fructose:sucrose=1:1:1 on weight basis, with a total of about 70 wt % of fructose, glucose and sucrose. The results are shown in table 1, obtained directly after heat treatment.

The results revealed that higher pH gives rise to Maillard reaction, thus reducing the LF retention. At low pH, hydrolytic reaction may occur. Optimum pH is around 3-3.5.

TABLE 1

LF retention at different pHs

| Sample | pH | % LF retention | % LF lost |
|---|---|---|---|
| Sample 1 | 2.4 | 90.3 | 9.7 |
| Sample 2 | 3.4 | 92.6 | 7.4 |
| Sample 3 | 4.2 | 84.7 | 15.3 |

LF retention: % of LF present in the sample, compared to the same sample before heat treatment, measured with the same analysis method.

Comparative Example I

Storage Temperature for LF with and Without Sugar

The storage stability of 1 wt % LF in syrup solution A (46% solids) after heat-treatment (95° C. for 45 seconds) was compared with normal LF aqueous solution at same pH (pH 3.5) at low and high storage temperatures, after heat-treatment at 95° C. for 45 seconds). Storage time was 2 weeks.

Results are shown in table 2. It was found that the LF concentration in syrup remained relatively constant, while LF in aqueous solution decayed relatively fast at higher storage temperature. It was concluded that the presence of sugar has a protective effect.

TABLE 2

Storage stability of LF

| Sample | LF-syrup solution (pH 3.5)** | LF aqueous solution (pH 3.5)** |
|---|---|---|
| t = 0* | 100% | 100% |
| 2 weeks (7° C.) | 95% | 96.1% |
| 2 weeks (37° C.) | 91% | 48.1% |

*Directly after heat treatment
**pH was adjusted with citric acid

Example 2

Storage Time

The long term storage stability of 1 wt % LF in 45% aqueous glucose solution was studied over a period of 4 months, after a heat treatment of 90° C. for 5 minutes. The storage temperature was 7° C.

It was found that the LF concentration remained unchanged, at a level of approximately 100%.

Comparative Example II

Analysis Methods (HPLC vs. FPLC) of LF % Without Sugar

4% Bovine LF solution (DMV, The Netherlands) in aqueous solution at pH 3.5 was subjected to heat treatment at 95° C. for different intervals (5, 10, 20 and 60 minutes). After heat treatment, the LF concentration was analysed for activity using FPLC (fast performance liquid chromatography) and HPLC (high performance liquid chromatography; "Morinaga" method).

The results are shown in table 3. It was found that FPLC differentiates between native LF and denatured LF, while HPLC, as used in the art (EP-A-437.958), systematically overestimates the concentration of native LF. Hence, the latter does not provide a satisfactory tool for LF analysis.

TABLE 3

Comparison of methods in analyzing LF content using HPLC vs. FPLC

| Heating time (min) | LF % (FPLC)[a] | LF % (HPLC)[b] |
|---|---|---|
| 0 | 100% | 100% |
| 5 | 97% | 104% |
| 10 | 95% | 103% |
| 20 | 94% | 104% |
| 60 | 75% | 93% |

[a]FPLC method performed in accordance with Mitoma et al. (2001): The J. Biol. Chem. 276: 18060-18065;
[b]HPLC method performed in accordance with Abe et al. (1991) J. Dairy Sci. 74: 65-71;

Comparative Example III

Effect of Sugar Content

The protective effect of sugar during the heat-treatment (at 95° C., for different time intervals) was studied by iso-electro-focusing gel electrophoresis between pH 3 and 9.

Results are shown in FIG. 1. From left to right: 5% bovine LF solution (pH 3.5), heat-treated at 90° C. for 5, 20 and 72 minutes; 5% bovine LF solution (pH 3.5) in 42% glucose solution (pH 3.5), heat-treated at 90° C. for 5, 20 and 72 minutes.

It was found that LF in sugar solution was more protected than that in aqueous solution without sugar: gel electrophoresis showed that the band for 5 wt % LF remained unchanged even after 20 minutes heat-treatment at 90° C., in case of 42 wt % sugar content. In contrast, the band for LF in aqueous solution without sugar shifted to a pH range more than pH 9.

Concluding, the use of sugar solution during the heat-treatment is able to endow the LF solution not only long shelf-life but also protect LF from deactivation by extended heat-treatment.

For sake of completeness, it is noted that a heat treatment of 95° C. for 72 minutes is not very realistic.

Comparative example IV

Effect of Sugar Content

Three 1% LF solutions were provided at pH 3.7 (using citrate and bicarbonate) with different sucrose concentrations, at 0%, 15% and 40%. The compositions were subjected to heating at 93° C.

At different times (after 0, 10, 35 and 72 minutes of heating) samples were taken and compared in terms of colour change over time. It was observed that the original reddish colour (at t=0) got lost in cases of 0% and 15% sugar, already within 10 minutes. This indicates LF denaturation. At 40% sugar levels, much of the original red colour was maintained, even after 75 minutes of heating. This reflects the storage stability of the LF heat-treated at a pH and sugar content according to the invention.

Figure 2B:
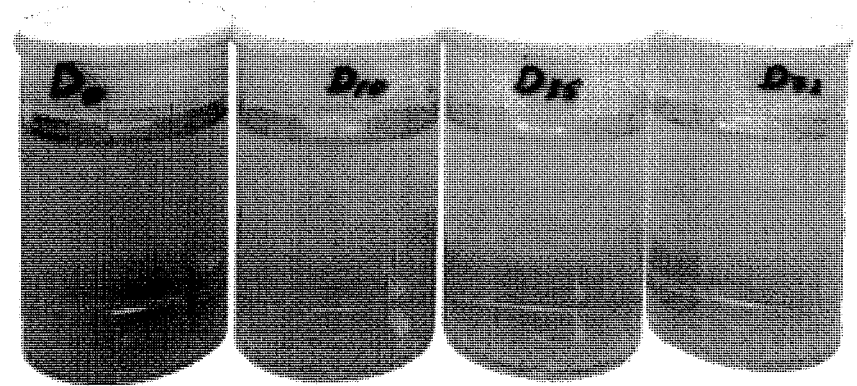
Figure 2C:
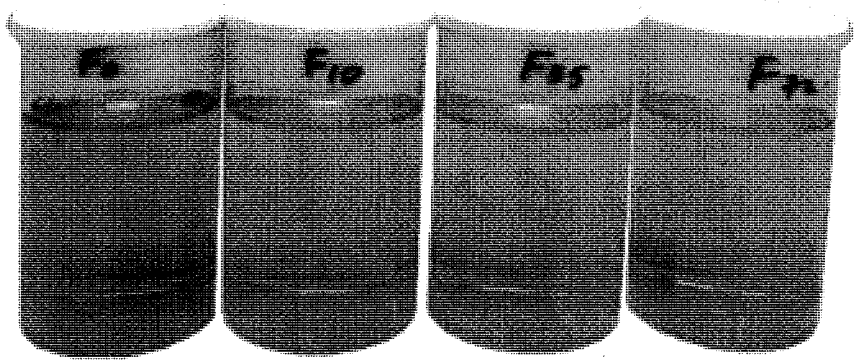

The attached FIG. 2 shows the differences among the samples described above, where (A), (B) and (C) stand for 0% (control), 15% and 40% of sugars, respectively. In each picture, going from left to right, samples are compared as taken after 0, 10, 35 and 72 minutes, respectively. All samples are taken at 1% LF content.

Example 3

Analysis Methods II

The active LF content was determined using FPLC, Elisa and iron-binding activity tests to study applicability of both analysis methods. The LF-containing syrup contained 0.26 wt % LF, 42% solids syrup A, and was heat-treated at 90° C. for 5, 20, and 60 minutes. Samples were taken and analyzed for LF retention and functionally active LF at different time intervals. The results are shown in table 4.

It was found that FPLC is a reliable method in evaluating LF activity, since the results closely matched those found using well-established Elisa. The concentration of LF was overestimated using iron binding assay. A possible explanation for any discrepancies may rest in the fact that at prolonged heat-treatment LF loses its native structure, thus changing retention time with FPLC, while its iron binding activity is maintained.

TABLE 4

LF retention (%) using FPLC, Elisa and Iron binding assay

| Sample | Heating time (min) | Elisa[a] | FPLC | Iron binding activity[b] |
|---|---|---|---|---|
| 1 | 0 | 100% | 100% | 100% |
| 2 | 5 | 87% | 80% | 97% |
| 3 | 20 | 51% | 56% | 94% |
| 4 | 60 | 17% | 29% | 65% |

[a]Bovine Lactoferrin ELISA Kit purchased from Biocompare. The method refers to Cheng et al. (2007) J. Dairy Sci. 91: 970-976
[b]Iron binding activity measurements performed in accordance with Brisson et al. (2007) International Dairy Journal .17: 617-624.

The invention claimed is:

1. A heat-treated liquid aqueous composition having a pH of 2-5, comprising:
   (a) lactoferrin and
   (b) 35-70 wt %, based on the total weight of the aqueous composition, carbohydrate and/or polyol stabilizers,
   wherein the composition has been subjected to a temperature of at least 60° C. and is a liquid at 20° C.

2. The composition according to claim 1, which has been sterilized or cooked.

3. The composition according to claim 1, wherein said carbohydrate and/or polyol stabilizer is selected from the group consisting of monosaccharides, disaccharides, trisaccharides, tetrasaccharides, pentasaccharides, hexasaccharides, oligosaccharides, mannitol, galactitol, inositol, xylitol, sorbitol, glycerol and lactitol, and mixtures thereof.

4. A heat-treated liquid aqueous composition having a pH of 2-5, comprising:
   (a) lactoferrin, (b) 35-70 wt. % of carbohydrate and/or polyol stabilizers based on the total weight of the aqueous composition, and (c) at least 45% glucose and fructose monosaccharides, wherein the composition has been subjected to a temperature of at least 60° C. and is a liquid at 20° C.

5. The composition according to claim 1, comprising, based on the total weight of the aqueous composition, 0.05-20 wt % lactoferrin.

6. The composition according to claim 5, comprising, based on the total weight of the aqueous composition, 0.05-10 wt % lactoferrin.

7. A heat-treated liquid aqueous composition having a pH between 2.5-4, comprising:
(a) heat-stabilized lactoferrin, and
(b) 35-70 wt. % of carbohydrate and/or polyol stabilizers based on the total weight of the aqueous composition, said composition having been subjected to a temperature of at least 60° C. and is a liquid at 20° C.

8. A method of preparing a liquid aqueous lactoferrin composition according to claim 1, comprising:
subjecting an aqueous composition having a pH of 2-5 and comprising lactoferrin, 35-70 wt % carbohydrate and/or polyol stabilizers based on the total weight of the aqueous composition, to a heat treatment of at least 60° C.

9. A method of treating acne, comprising administering to a subject in need thereof a composition according to claim 1.

10. The composition according to claim 1, comprising 40-65 wt. % of carbohydrate and/or polyol stabilizers based on the total weight of the aqueous composition.

11. The composition according to claim 1, comprising 1-15 wt. % of lactoferrin based on the total weight of the aqueous composition.

12. The composition according to claim 1, comprising 2-10 wt. % of lactoferrin based on the total weight of the aqueous composition.

* * * * *